US006190692B1

(12) United States Patent
Busetti et al.

(10) Patent No.: US 6,190,692 B1
(45) Date of Patent: Feb. 20, 2001

(54) TIME-SPECIFIC CONTROLLED RELEASE CAPSULE FORMULATIONS AND METHOD OF PREPARING SAME

(76) Inventors: Cesare Busetti, Via Signorini 7, Milano (IT), 20149; Tiziano Crimella, Via Londinio 1, Milano (IT), 20154

( * ) Notice: Under 35 U.S.C. 154(b), the term of this patent shall be extended for 0 days.

(21) Appl. No.: 08/991,814

(22) Filed: Dec. 16, 1997

Related U.S. Application Data

(63) Continuation-in-part of application No. 08/790,530, filed on Jan. 29, 1997, now Pat. No. 5,891,474.

(51) Int. Cl.[7] ................................ A61K 9/48; A61K 9/14

(52) U.S. Cl. .......................... 424/451; 424/490; 424/489; 424/480

(58) Field of Search .................................... 424/451, 490, 424/489, 480

(56) References Cited

U.S. PATENT DOCUMENTS

| | | | |
|---|---|---|---|
| 3,131,123 | 4/1964 | Masquelier | 167/57 |
| 4,432,966 | 2/1984 | Zeitoun et al. | 424/21 |
| 4,683,092 | 7/1987 | Tsang | 264/4.3 |
| 4,713,248 | 12/1987 | Kjørnæs et al. | 424/468 |
| 4,729,893 | 3/1988 | Letcher et al. | 424/98 |
| 4,777,089 | 10/1988 | Takizawa et al. | 428/402.22 |
| 4,780,318 | 10/1988 | Appelgren et al. | 424/469 |
| 4,786,505 | 11/1988 | Lovgren et al. | 424/468 |
| 4,786,506 | 11/1988 | Fontanelli | 424/470 |
| 4,795,643 | 1/1989 | Seth | 424/456 |
| 4,844,905 * | 7/1989 | Ichikawa et al. | 424/451 |
| 4,851,231 | 7/1989 | Urquhart et al. | 424/469 |
| 4,853,230 | 8/1989 | Lovgren et al. | 424/466 |
| 4,853,249 | 8/1989 | Takashima et al. | 427/3 |
| 4,857,335 | 8/1989 | Bohm | 424/455 |
| 4,857,337 | 8/1989 | Miller et al. | 424/480 |
| 4,863,742 | 9/1989 | Panoz et al. | 424/473 |
| 4,871,549 | 10/1989 | Ueda et al. | 424/494 |
| 4,882,169 | 11/1989 | Ventouras | 424/493 |
| 4,886,669 | 12/1989 | Ventouras | 424/469 |
| 4,888,179 | 12/1989 | Appelgren et al. | 424/480 |
| 4,910,021 | 3/1990 | Davis et al. | 424/456 |
| 4,917,892 | 4/1990 | Speaker et al. | 424/401 |
| 4,923,645 | 5/1990 | Tsang et al. | 264/4.3 |
| 4,971,805 | 11/1990 | Kitanishi et al. | 424/494 |
| 5,007,790 * | 4/1991 | Shell | 424/451 |
| 5,035,899 | 7/1991 | Saeki et al. | 424/480 |
| 5,084,278 | 1/1992 | Mehta | 424/441 |
| 5,089,269 | 2/1992 | Noda et al. | 424/456 |
| 5,096,717 | 3/1992 | Wirth et al. | 424/490 |
| 5,175,003 | 12/1992 | Goldman | 424/484 |
| 5,217,720 | 6/1993 | Sekigawa et al. | 424/480 |
| 5,232,706 | 8/1993 | Palomo Coll | 424/475 |
| 5,238,686 | 8/1993 | Eichel et al. | 424/461 |
| 5,262,172 * | 11/1993 | Sipos | 424/490 |
| 5,273,760 | 12/1993 | Oshlack et al. | 424/480 |
| 5,275,824 | 1/1994 | Carli et al. | 424/490 |
| 5,294,448 | 3/1994 | Ring et al. | 424/497 |
| 5,296,233 | 3/1994 | Batista et al. | 424/463 |
| 5,302,400 | 4/1994 | Sipos | 424/494 |
| 5,316,772 | 5/1994 | Jurgens, Jr. et al. | 424/472 |
| 5,330,835 | 7/1994 | Kikuchi et al. | 424/402.22 |
| 5,378,474 | 1/1995 | Morella et al. | 424/469 |
| 5,395,626 | 3/1995 | Kotwal et al. | 424/472 |
| 5,445,829 | 8/1995 | Paradissis et al. | 424/480 |
| 5,464,633 | 11/1995 | Conte et al. | 424/480 |
| 5,482,718 | 1/1996 | Shah et al. | 424/480 |
| 5,498,422 | 3/1996 | Nakamichi et al. | 424/451 |
| 5,510,119 | 4/1996 | Santus et al. | 424/490 |
| 5,514,384 | 5/1996 | Signorino | 424/490 |
| 5,527,545 | 6/1996 | Santus et al. | 424/490 |
| 5,536,507 | 7/1996 | Abramowitz et al. | 424/479 |
| 5,614,218 | 3/1997 | Olsson et al. | 424/456 |
| 5,614,220 | 3/1997 | Hirakawa et al. | 424/480 |
| 5,616,345 | 4/1997 | Geoghegan et al. | 424/497 |
| 5,637,320 | 6/1997 | Bourke et al. | 424/489 |
| 5,654,004 | 8/1997 | Okayama et al. | 424/479 |

FOREIGN PATENT DOCUMENTS

| | | | |
|---|---|---|---|
| 0 305 918 | 8/1988 | (EP) | A61K/9/54 |
| 0 366 621 | 10/1989 | (EP) | A61K/9/54 |
| 0 453 001 | 1/1991 | (EP) | A61K/9/24 |
| 572 942 | 5/1993 | (EP) | A61K/9/28 |
| 0 629 398 | 6/1994 | (EP) | A61K/9/50 |

OTHER PUBLICATIONS

Gazzaniga, A. et al., "Time–dependent oral delivery systems for colon targeting," *S.T.P. Pharm Sci.* 5(1) :83–88 (1995).

Nishimura, K. et al., "Dosage Form Design for Improvement of Bioavailability of Levodopa VI: Formulation of Effervescent Enteric–Coated Tablets," *J. Pharm. Sci.* 73 (7) :942–946 (1984).

* cited by examiner

*Primary Examiner*—Thurman K. Page
*Assistant Examiner*—Isis Ghali
(74) *Attorney, Agent, or Firm*—Townsend & Townsend & Crew

(57) ABSTRACT

The present invention provides a method of achieving the time-specific delivery of a pharmaceutically active agent to a patient in need of the therapeutic effects of the pharmaceutically active agent. The method includes administering a pharmaceutical formulation comprising (a) a core including the pharmaceutically active agent to be delivered, and (b) a swellable polymeric coating layer substantially surrounding the core. The swellable polymeric coating layer delays the release of the pharmaceutically active agent from the core for a predetermined period of time dependent upon the thickness of the swellable polymeric coating layer. The swellable polymeric coating layer surrounding the core is provided by a new method which includes alternately (I) wetting the core with a binder solution, and (ii) coating the core with powdered polymeric particles a sufficient number of times to produce a time-specific dosage formulation having the desired thickness of swellable polymeric coating layer.

20 Claims, No Drawings

TIME-SPECIFIC CONTROLLED RELEASE CAPSULE FORMULATIONS AND METHOD OF PREPARING SAME

RELATED APPLICATION

The instant application is a continuation-in-part application U.S. patent application Ser. No. 08/790,530, filed Jan. 29 1997 is now 5,891,474, to which a claim of priority is asserted. The subject matter of parent application Ser. No. 08/790,530 is incorporated herein by reference in its entirety.

FIELD OF THE INVENTION

The present invention relates to controlled release dosage formulations. More particularly, the present invention relates to a method of preparing a time-specific controlled release dosage formulations.

BACKGROUND OF THE INVENTION

Pharmaceutical formulations for oral administration have employed various coatings for the purpose of preserving the integrity of the formulation while passing through the gastric tract. The high acidity, and presence of proteolytic and other enzymes generates a highly digestive environment which readily disintegrates pharmaceutical formulations which do not possess some type of gastro-resistance protection.

In recent years, a need has arisen for formulations which are capable of passing over the entire tract of the small intestine, including the duodenum, jejunum, and ileum, so that the active ingredients are released directly in the colon. For example, European Patent Application No. 366 621 provides a formulation for delivery in the colon which includes a core containing the active ingredient and three protective layers having differing solubilities around the core. As another example, our European Application No. 572 942, disclosure of which is hereby incorporated by reference in its entirety, provides an oral pharmaceutical composition including a core containing the active ingredient, an intermediate coating layer which delays the release of the active ingredient contained in the core for a programmed time period, and an outer layer, the dissolution of which activates the process of swelling/dissolution/erosion of the intermediate layer. In the composition described in European Application No. 572 942, the coating layers are applied sequentially by watery or organic film coating or by press coating techniques, such as double press coating. A primary disadvantage of these coating methods is that these methods employ solutions of the coating polymers, which coating polymers have very high viscosities in water-based environments.

Double press coating techniques have some disadvantages in that the core of the formulation may not be properly centered within the coating, and a relatively large amount of polymer is required for proper coating.

There also remains a need in the art for pharmaceutical formulations which release active ingredient after a predetermined latency or lag time period in the body, i.e., time-specific release formulations.

SUMMARY OF THE INVENTION

It is therefore an object of the present invention to provide a method of preparing a time-specific release pharmaceutical formulation which is faster than conventional coating techniques. It is also an object of the present invention to provide a time-specific pharmaceutical formulation, the disintegration of which is triggered by time lapse, independently of the pH of the environment to which it is subjected.

As a first aspect, the present invention provides a method of achieving the time-specific delivery of a pharmaceutically active agent to a patient in need of the therapeutic effects of the pharmaceutically active agent. The method includes administering a pharmaceutical formulation comprising (a) a core including the pharmaceutically active agent to be delivered, and (b) a swellable polymeric coating layer substantially surrounding the core. The swellable polymeric coating layer delays the release of the pharmaceutically active agent from the core for a predetermined period of time dependent upon the thickness of the swellable polymeric coating layer.

As a second aspect, the present invention provides a method of providing the swellable polymeric coating layer surrounding the core. The method includes alternately (I) wetting the core with a binder solution, and (ii) coating the core with powdered polymeric particles a sufficient number of times to produce a time-specific dosage formulation having the desired thickness of swellable polymeric coating layer.

As a third aspect, the present invention provides another method for time-specific delivery of a pharmaceutically active agent to a patient in need of the therapeutic effects of the pharmaceutically active agent. The method comprises administering a pharmaceutical formulation comprising (a) a core including the pharmaceutically active agent, and (b) a swellable polymeric coating layer substantially surrounding the core, that delays the release of the pharmaceutically active agent from the core for a predetermined period of time dependent upon the thickness of the swellable polymeric coating layer. The swellable polymeric coating layer is formed from powdered polymeric particles.

As a fourth aspect, the present invention provides a method for producing a time-specific dosage formulation for the time-specific delivery of a pharmaceutically active agent. The method comprises coating a core containing the pharmaceutically active agent with a swellable polymeric coating layer that delays the release of the pharmaceutically active agent from the core for a predetermined period of time dependent upon the thickness of the swellable polymeric coating layer. The step of coating the core with the swellable polymeric coating layer comprises alternately (I) wetting the core with a binder solution, and (ii) coating the core with powdered polymeric particles a sufficient number of times to produce a time-specific dosage formulation having the desired thickness of swellable polymeric coating layer.

As a fifth aspect, the present invention provides another method for time-specific delivery of a pharmaceutically active agent to a patient in need of the therapeutic effects of the pharmaceutically active agent. The method comprises administering to the patient, a pharmaceutical formulation comprising: (a) a core which comprises a capsule containing a liquid form of the pharmaceutically active agent, and (b) a swellable polymeric coating layer substantially surrounding the core. The swellable polymeric coating layer delays the release of the pharmaceutically active agent from the core for a predetermined period of time dependent upon the thickness of the swellable polymeric coating layer. The swellable polymeric coating layer is provided by alternately (I) wetting the core with a binder solution, and (ii) coating the core with powdered polymeric particles a sufficient number of times to produce a time-specific dosage formulation having the desired thickness of swellable polymeric coating layer.

As a sixth aspect, the present invention provides yet another method for time-specific delivery of a pharmaceutically active agent to a patient in need of the therapeutic effects of the pharmaceutically active agent. The method comprises administering a pharmaceutical formulation comprising: (a) a core which comprises a capsule containing a liquid form of the pharmaceutically active agent, and (b) a swellable polymeric coating layer substantially surrounding the core. The swellable polymeric coating delays the release of the pharmaceutically active agent from the core for a predetermined period of time dependent upon the thickness of the swellable polymeric coating layer. The swellable polymeric coating layer is formed from powdered polymeric particles.

As a seventh aspect, the present invention provides another method for producing a time-specific dosage formulation for time-specific delivery of a pharmaceutically active agent. The method comprises coating a core comprising a capsule containing a liquid form of the pharmaceutically active agent, with a swellable polymeric coating layer that delays the release of the pharmaceutically active agent from the core for a predetermined period of time dependent upon the thickness of the swellable polymeric coating layer. The step of coating the core with the swellable polymeric coating layer comprises alternately (I) wetting the core with a binder solution, and (ii) coating the core with powdered polymeric particles a sufficient number of times to produce a time-specific dosage formulation having the desired thickness of swellable polymeric coating layer. The core can be provided by the steps of (1) providing a liquid form of the pharmaceutically active agent, which form is selected from the group consisting of solutions, liposome dispersions, oil-in-water emulsions, microemulsions, precursors of microemulsions and liposomes, dispersions of microparticles, dispersions of nanoparticles, dispersions of solid lipid nanoparticles, and suspensions, and (2) encapsulating the liquid form of the pharmaceutically active agent in a capsule, prior to coating the core with the swellable polymeric coating layer.

As another aspect, the present invention provides a pharmaceutical formulation for the time-specific delivery of a pharmaceutically active agent. The formulation comprises: (a) a core which comprises a capsule containing a liquid form of the pharmaceutically active agent, and (b) a swellable polymeric coating layer substantially surrounding the core. The swellable polymeric coating layer delays the release of the pharmaceutically active agent from the core for a predetermined period of time dependent upon the thickness of the swellable polymeric coating layer. The swellable polymeric coating layer is provided by alternately (I) wetting the core with a binder solution, and (ii) coating the core with powdered polymeric particles a sufficient number of times to produce a time-specific dosage formulation having the desired thickness of swellable polymeric coating layer.

The foregoing and other objects and aspects of the present invention are explained in detail in the detailed description and examples set forth hereinbelow. References referred to herein are incorporated into the present application by reference in their entirety.

DETAILED DESCRIPTION OF THE INVENTION

The methods of the present invention may be employed to achieve the time-specific release of a pharmaceutically active agent and to provide a time-specific controlled-release pharmaceutical formulation for pharmaceutically active agents which are desirously delivered after a predetermined period of time. Suitable pharmaceutically active agents which can be administered by using the methods and formulations of the present invention include pharmaceutically active agents which can be formulated in either solid dosage forms such as tablets, caplets, and capsules as well as pharmaceutically active agents which can be formulated in liquid forms, particularly as liquid-filled capsules. Thus, the methods and formulations of the present invention are suitable for administration of a wide variety of pharmaceutically active agents. More specifically, pharmaceutically active agents which may be employed in the methods of the present invention include, but are not limited to:

steroids such as betamethasone, dexamethasone, methylprednisolone, prednisolone, prednisone, triamcinolone, budesonide, hydrocortisone, and pharmaceutically acceptable hydrocortisone derivatives;

xanthines such as theophylline and doxophylline;

beta-2-agonist bronchodilators such as salbutamol, fenterol, clenbuterol, bambuterol, salmeterol, fenoterol;

antiinflammatory agents, including antiasthmatic antiinflammatory agents, antiarthritis antiinflammatory agents, and non-steroidal antiinflammatory agents, examples of which include but are not limited to sulfides, mesalamine, budesonide, salazopyrin, diclofenac, pharmaceutically acceptable diclofenac salts, nimesulide, naproxene, acetominophen, ibuprofen, ketoprofen and piroxicam;

analgesic agents such as salicylates;

calcium channel blockers such as nifedipine, amlodipine, and nicardipine;

angiotensin-converting enzyme inhibitors such as captopril, benazepril hydrochloride, fosinopril sodium, trandolapril, ramipril, lisinopril, enalapril, quinapril hydrochloride, and moexipril hydrochloride;

beta-blockers (i.e., beta adrenergic blocking agents) such as sotalol hydrochloride, timolol maleate, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate;

centrally active alpha-2-agonists such as clonidine;

alpha-1-antagonists such as doxazosin and prazosin;

anticholinergic/antispasmodic agents such as dicyclomine hydrochloride, scopolamine hydrobromide, glycopyrrolate, clidinium bromide, flavoxate, and oxybutynin;

vasopressin analogues such as vasopressin and desmopressin;

antiarrhythmic agents such as quinidine, lidocaine, tocainide hydrochloride, mexiletine hydrochloride, digoxin, verapamil hydrochloride, propafenone hydrochloride, flecainide acetate, procainamide hydrochloride, moricizine hydrochloride, and disopyramide phosphate;

antiparkinsonian agents, such as dopamine, L-Dopa/Carbidopa, selegiline, dihydroergocryptine, pergolide, lisuride, apomorphine, and bromocryptine;

antiangina agents and antihypertensive agents such as isosorbide mononitrate, isosorbide dinitrate, propranolol, atenolol and verapamil;

- anticoagulant and antiplatelet agents such as coumadin, warfarin, acetylsalicylic acid, and ticlopidine;
- sedatives such as benzodiazapines and barbiturates;
- ansiolytic agents such as lorazepam, bromazepam, and diazepam;
- peptidic and biopolymeric agents such as calcitonin, leuprolide and other LHRH agonists, hirudin, cyclosporin, insulin, somatostatin, protirelin, interferon, desmopressin, somatotropin, thymopentin, pidotimod, erythropoietin, interleukins, melatonin, granulocyte/macrophage-CSF, and heparin;
- antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride;
- laxatives such as senna concentrate, casanthranol, bisacodyl, and sodium picosulphate;
- antidiarrheal agents such as difenoxine hydrochloride, loperamide hydrochloride, furazolidone, diphenoxylate hdyrochloride, and microorganisms;
- vaccines such as bacterial and viral vaccines;
- antimicrobial agents such as penicillins, cephalosporins, and macrolides'
- antifungal agents such as imidazolic and triazolic derivatives; and
- nucleic acids such as DNA sequences encoding for biological proteins, and antisense oligonucleotides.

The cores employed in the methods of the present invention may be either solid, tablet-like cores or liquid filled capsule cores. In the case of solid, tablet-like cores, the cores typically include one or more pharmaceutically acceptable excipients in addition to the pharmaceutically active agent. Pharmaceutically acceptable excipients which may be employed are well known to those skilled in the art and include any conventional pharmaceutically acceptable tableting excipients. Examples of suitable excipients include but are not limited to microcrystalline cellulose, dibasic calcium phosphate dihydrate, starch, sodium starch glycolate, crospovidone, croscarmellose sodium, magnesium stearate, lactose, maleic acid, colloidal silicon dioxide, talc, and glyceryl behenate.

The core can be prepared by any suitable technique known to those skilled in the art. For example, the pharmaceutically active agent may be admixed with the excipient(s) and advantageously formed into a tablet or caplet using a conventional tableting press.

In the embodiment wherein the core is a capsule containing a liquid form of the pharmaceutically active agent, the pharmaceutically active agent is provided in a liquid form such as a solutions, liposome dispersions, oil-in-water emulsions, microemulsions, precursors of microemulsions and liposomes, dispersions of microparticles, dispersions of nanoparticles, dispersions of solid lipid nanoparticles, and suspensions. Any conventional technique for providing the active in the form of a solution, liposome dispersions, oil-in-water emulsion, microemulsion, precursors of microemulsion and/or liposomes, dispersions of microparticles, dispersions of nanoparticles, dispersions of solid lipid nanoparticle, or suspension can be employed. Generally, liquid forms of a pharmaceutically active agent can be provided by bringing into association the pharmaceutically active agent and one or more carriers such as by solubilizing, dispersing, or suspending the pharmaceutically active agent in a suitable carrier or emulsifying a liquid containing the pharmaceutically active agent. Of course suitable carriers will be those carriers which do not interfere with the activity of the particular pharmaceutically active agent to be administered, and are pharmaceutically acceptable in the sense that they are not deleterious to the patient to which the formulation will be administered.

Suitable carriers include hydrophilic and lipophilic carriers include, for example, pharmaceutically acceptable alcohols such as ethanol; glycols such as ethoxy diglycol, ethylene glycol, propylene glycol, and polyethylene glycols of varying length (e.g., PEG-4, PEG-6, PEG-8, etc.); alkyl esters of fatty acids such as isopropyl myristate, isopropyl palmitate, isopropyl stearate, isopropyl oleate, and polyglyceryl-6 isostearate; mono-, di-, and triglycerides; polyoxyethylene-polyoxypropylene thermosetting copolymers; phospholipids such as phosphatidylcholine; natural and synthetic oils such as hydrogenated coconut oil, palm oil, corn oil, almond oil, white mineral oil, silicon oil, dimethylpolysiloxane; propylene glycol dipelargonate; trilaneth-4-phosphate. Other examples of conventional, suitable hydrophilic and lipophilic carriers which may be employed for the productions of liquid forms of any of the above-listed pharmaceutically active agents can be found in REMINGTON'S PHARMACEUTICAL SCIENCES, 18th ed. A. Gennaro, Mack Publishing Co., Easton Pa. (1990). In some instances it may be desirable to combine two or more hydrophilic carriers, two or more lipophilic carriers, or a combination of an hydrophilic and lipophilic carriers to provide the pharmaceutically active agent in liquid form.

The liquid form of the pharmaceutically active agent may also contain additives such as, for example, conventional dispersants, preservatives, stabilizers, surfactants, antioxidants, buffers, colorants, and the like, as will be understood by those skilled in the art of pharmacy.

Further advantages of the formulation are obtained by including in the liquid form components such as enhancers to improve the intestinal absorption of specific active agents, or enzyme-inhibitors to protect specific active agents from intestinal enzymatic degradation.

The pharmaceutically active agents may be formulated into a liquid form using any suitable, conventional techniques known to those skilled in the art of pharmacy. REMINGTON'S PHARMACEUTICAL SCIENCES, 18th ed. A. Gennaro, Mack Publishing Co., Easton Pa. (1990) as well as many other general pharmacy texts described methods for formulating active agents in solutions, liposome dispersions, oil-in-water emulsions, microemulsions, precursors of microemulsions and/or liposomes, dispersions of microparticles, dispersions of nanoparticles, dispersions of solid lipid nanoparticles, and suspensions; which methods may be employed to provide the pharmaceutically active agent in liquid form according to the present invention.

For example, solutions containing pharmaceutically active agents can be produced by substantially completely solubilizing the pharmaceutically active agent in a suitable carrier, optionally with stirring and/or the addition of heat.

Emulsions may be obtained by solubilizing the pharmaceutically active agent in either an aqueous or an oil phase and emulsifying the aqueous and oil phases with the aid of at least one surfactant.

The liposome dispersions may be produced according to conventional techniques, through the use of phospholipids after the solubilization of the pharmaceutically active agent. Suitable conventional techniques for the production of liposome dispersions are described in Martindale, 18th Edition, page 1691–1692; *Pharmaceutical Manufacturing of*

*Liposomes,* F. J. Martin, SPECIALIZED DRUG DELIVERY SYSTEMS, Marcel Dekker Inc., pg. 267–316; and *Specialized Pharmaceutical Emulsions,* M. Rosoff, PHARMACEUTICAL DOSAGE FORMS: DISPERSE SYSTEMS, vol. 1, Marcel Dekker Inc., pg 245–283.

Microemulsions may be obtained as described in Martindale, 18th Ed., pg 1536; and *Specialized Pharmaceutical Emulsions,* M. Rosoff, PHARMACEUTICAL DOSAGE FORMS: DISPERSE SYSTEMS, vol. 1, Marcel Dekker Inc., pg 245–283.

Precursors of microemulsions and liposomes may be obtained in the same way as microemulsions and liposome dispersions, but with less, or no quantity of water.

Microparticles may be obtained as described in Martindale, 18th Edition, page 1663–1664; and *Microencapsulation: Scale-Up Considerations and Production Technology,* V. A. Crainich, SPECIALIZED DRUG DELIVERY SYSTEMS, Marcel Dekker Inc., pg. 221–255. Dispersions of these microparticles can then be obtained using the dispersion techniques described above.

Nanoparticles may be obtained as described in Martindale, 18th Edition, page 1691; and *Large-Scale Production Problems and Manufacturing of Nanoparticles,* J. Kreuter, SPECIALIZED DRUG DELIVERY SYSTEMS, Marcel Dekker Inc., pg. 257–266. Dispersions of these nanoparticles can then be obtained using the dispersion techniques described above.

Solid lipid nanoparticles may be obtained as described in *Nanoparticelle Lipidiche Solide Quali Sistemi Terapeutici Colloidali,* M. R. Gasco, NCF nr. 7, 1996, pg 71–73. Dispersions of these particles can then be obtained using the dispersion techniques described above.

Suspensions may be obtained by suspending the pharmaceutically active agent in a carrier in which it is partially, substantially, or completely insoluble.

The pharmaceutically active agent in liquid form is then encapsulated in a capsule prior to coating the capsule core with the swellable polymeric coating layer by filling the capsule with the liquid form of the pharmaceutically active agent and sealing the capsule to contain the liquid. Any conventional pharmaceutical capsule may be employed. Examples of suitable capsules include gelatin-based capsules (both hard and soft), starch-based capsules, and vegetable-based capsules. Currently soft shell gelatin capsules are preferred for the methods of the present invention. When gelatin or starch capsules are employed, the liquid form of the pharmaceutically active agent preferably includes lipophilic carriers, and in some instances, also hydrophilic carriers in an amount which does not cause the solubilization of the gelatin or starch capsule by the carrier. Typically, the amount of hydrophilic carrier is not more than 30% in those formulations which include by a hydrophilic and a lipophilic carrier. However, this number will differ depending upon the particular capsules employed. Capsule manufacturers typically establish the maximum amount of hydrophilic carrier which can be suitable encapsulated within their particular capsules.

According to the methods of the present invention, the pre-formed core, whether it is a solid, tablet-like core or a liquid filled capsule core, is substantially surrounded by a swellable polymeric coating layer. The swellable polymeric coating layer delays the release of the pharmaceutically active agent for a predetermined period of time, which period of time is dependent upon the thickness of the swellable polymeric coating layer. In other words, the thicker the swellable polymeric coating, the longer it delays the release of the active ingredient from the core of the formulation. Thus, the appropriate time period for the release of the active ingredient can be determined prior to the preparation of the formulation, and the formulation designed by applying the appropriate thickness of swellable polymeric coating layer to achieve the desired time delay prior to release of the active ingredient. Typically, the desired time delay will range from about 4 to about 9 hours inclusive, but may be longer or shorter in certain cases.

Because the formulations of the present invention provide the time-delayed release of a pharmaceutically active agent, the formulations provided by the instant invention are useful for the treatment of conditions which are desirously treated through time-delayed pharmaceutical agent delivery mechanisms. For example, the formulations of the present invention are useful for the treatment of morning pathologies, i.e., pathologies, conditions, diseases, or other illnesses, the symptoms of which are generally pronounced, aggravated, or more acute in the morning as the afflicted subject awakens from sleep. The Inventors have filed concurrently herewith, a separate patent application directed toward methods of treating morning pathologies with the time-specific formulations of the present invention. Morning pathologies include arthritis, angina, hypertension, and asthma. These conditions may be advantageously treated by administering the time-specific formulation according to the present invention prior to sleeping such that the delivery of the pharmaceutically active agent is achieved at about the time the afflicted subject awakens, thereby alleviating the symptoms of the morning pathology.

The swellable polymeric coating layer is comprised of two basic components, a binder solution, and powdered polymeric particles. The swellable polymeric coating layer is applied to the core in a two-step fashion, which steps are repeated a sufficient number of times to build the thickness of the swellable polymeric coating layer. In the first step, the core is wet with the binder solution which serves to adhere the powdered polymeric coating particles to the wet core. Suitable binder solutions may include conventional pharmaceutically acceptable binder agents solubilized in a suitable solvent. Specific examples of binder agents include but are not limited to vinyl polymers, such as polyvinylpyrrolidone, polyvinyl alcohol, and the like; cellulosic polymers, such as hydroxypropylmethylcellulose, hydroxyethylcellulose, hydroxypropylcellulose, and the like; acrylic polymers and copolymers such as methacrylic acid copolymers, ethyl acrylate-methylmethacrylate copolymers, and the like; natural or synthetic gums, such as guar gum, arabic gum, xanthan gum, and the like; proteins or carbohydrates, such as gelatin, pectin, and the like; and mixtures thereof. Currently, polyvinylpyrrolidone is the preferred binder agent.

Suitable solvents for solubilizing the binder agents include solvents which are capable of substantially completely solubilizing the specific binder agent(s) selected and which are pharmaceutically and biologically acceptable for ingestion. Suitable solvents will be readily determinable by those skilled in the art. Water is currently the preferred solvent for solubilizing the binder agent, as it is pharmacologically and biologically well suited for ingestion. However, other examples of suitable solvents will be appreciated by those skilled in the art and are contemplated by the methods of the present invention.

The binder solution should be of sufficient viscosity to enable the wetting of the cores by any suitable wetting technique known to those skilled in the art. For example, the cores may be wetted with the binder solution by rotating the cores in a bath containing the binder solution. The cores may be suitably wetted by manual application of the binder solution by ladling the binder solution over the cores as the cores are rotating in a conventional coating pan. Alternatively, the cores may be wetted by spraying the binder solution on the cores. In one embodiment, the wetting step is advantageously carried out using conventional automated pan coating equipment wherein the cores are sprayed with the binder solution while rotating in the pan.

To provide the coating layer, the wetted cores are coated with dry, powdered polymeric coating particles which adhere to the binder-wetted core due to the presence of the binder on the surface of the core. The polymeric coating particles typically comprise a hydrophilic gelling polymer or "swellable" polymer which swells on contact with gastrointestinal juices to form a continuous film surrounding the core. The coating layer must sufficiently protect the integrity of the core for the desired period of time, without regard to the pH of the medium to which it is subjected. Once the desired, pre-delivery time period has elapsed, the coating layer should be almost completely dissolved or eroded so that the core should be capable of relatively quick disintegration. Thus, it is desirable that the core be capable of the fast, time-specific release of the pharmaceutically active agent. Significantly, the methods of the present invention do not required polymeric solutions for the formation of the swellable polymeric coating layer and as such provide distinct advantages in terms of ease of manufacture and decreased manufacturing time. Because the methods of the present invention do not utilize polymeric solutions for the formation of the swellable polymeric coating layer, but instead utilize dry powdered polymeric particles, polymers which exhibit high viscosity in solution may be used in the methods of the present invention although they may not be functional in conventional film coating methods.

The polymeric coating particles may be comprised of any suitable hydrophilic gelling polymer known to those skilled in the art. For example, suitable hydrophilic gelling polymers include but are not limited to cellulosic polymers, such as methylcellulose, carboxymethylcellulose, hydroxypropylcellulose, hydroxypropylmethylcellulose, hydroxyethylcellulose, and the like; vinyl polymers, such as polyvinylpyrrolidone, polyvinyl alcohol, and the like; acrylic polymers and copolymers, such as acrylic acid polymer, methacrylic acid copolymers, ethyl acrylate-methyl methacrylate copolymers, and the like; and mixtures thereof. Currently, the preferred polymeric particles comprise hydroxypropylmethylcellulose.

Hydroxypropylmethylcellulose is a polymer which is available in many forms, including forms of different molecular weight, extremely different viscosity and different substitution grade. The inventors have also discovered that it is advantageous in certain applications to utilize mixtures or blends of two or more different forms of hydroxypropylmethylcellulose as the polymeric coating particles. In one preferred embodiment, the polymeric coating particles of the coating layer comprise a mixture of polymeric coating particles having differing molecular weights and solubility characteristics. For example, the coating layer may be comprised of polymeric coating particles comprising a mixture of a) hydroxypropylmethylcellulose having I) a typical weight percent substitution corresponding to 29% methoxyl and 8% hydroxypropoxyl groups, and ii) a nominal viscosity of a 2% watery solution at 20° C. ranging from 5 to 100 mPa.s; and b) hydroxypropylmethylcellulose having I) a typical weight percent substitution corresponding to 22.1% methoxyl and 8.1% hydroxypropoxyl groups, and ii) a nominal viscosity of a 2% watery solution at 20° C. ranging from 4,000 to 100,000 mPa.s. An example of the first type of hydroxypropylmethylcellulose is METHOCEL E5®, and an example of the second type is METHOCEL K15M®, both of which are commercially available from Colorcon.

The polymer(s) of the swellable polymeric coating layer partially hydrates on the outer surface thereof after ingestion to form a gel-like layer that acts as a skin, controlling the rate of erosion of the coating layer. As a consequence, the release or delivery of the pharmaceutically active agent contained within the core is inhibited for the predetermined period of time.

Grades of hydroxypropylmethylcellulose having different degrees of substitution also possess different rates of hydration. The inventors have discovered that by utilizing mixtures or blends of two or more polymers with different rates of hydration, it is possible to obtain a layer with improved characteristics in terms of the rate-controlled hydration of the same.

Because the formulations and methods of the present invention may include either a single hydroxypropylmethylcellulose or a blend of two or more different forms of hydroxypropylmethylcellulose as the powdered polymeric coating particles, for simplicity, the term "hydroxypropylmethylcellulose" as used herein, including the claims, refers to either a single hydroxypropylmethylcellulose or a blend of two or more forms of the polymer.

Alternatively, the swellable polymeric coating layer may be comprising of other substances which are capable of becoming freely permeable with an exactly defined kinetic following hydration in aqueous fluids. Such substances include polysaccharides, such as gelatin, saccharose, sorbitol, mannanes, and jaluronic acid; polyaminoacids; polyalcohols; polyglycols; and the like.

In addition to the foregoing, the swellable polymeric coating layer may also include additional excipients such as lubricants, flow promoting agents, plasticizers, antisticking agents, natural and synthetic flavorings and natural and synthetic colorants. Specific examples of additional excipients include polyethylene glycol, polyvinylpyrrolidone, talc, magnesium stearate, glyceryl behenate, stearic acid, and titanium dioxide.

After the powdered polymeric coating particles are applied to the wetted core, the steps of first, wetting the core with binder and second, coating with powdered polymeric coating particles are repeated sequentially one or more additional times in order to build the thickness of the swellable polymeric coating layer around the core. In other words, the alternating steps of wetting the core and coating with powdered polymeric coating particles are repeated in alternate fashion so that prior to each application of the powdered coating particles, the core is first wetted with binder solution. In this manner of repeated alternate applications of binder solution and powdered polymeric coating particles, the thickness of the swellable polymeric coating layer is increased to the desired measure. The number of repeated wetting and coating cycles is dependent upon the desired predetermined time for delivery of the active ingredient. The thicker the swellable polymeric coating layer around the core, the longer the latency, or lag time prior to delivery of the active ingredient. Typically, a sufficient number of wetting and coating cycles are performed so as to produce a core:coating layer weight ratio of between about 20:1 and about 1:5 inclusive, or a thickness in excess of about 10 $\mu$m, and up to about 3 mm. Preferably, a sufficient number of coating cycles are completed so as to produce a core:coating layer weight ratio of between about 5:1 and about 1:3 inclusive, or a thickness of between about 50 $\mu$m and about 1.5 mm.

In an alternate embodiment of the present invention, the swellable polymeric coating layer may be applied to the core using conventional film (or spray) coating techniques or double press coating techniques which are known to those skilled in the art of pharmacy. In the embodiment wherein the swellable polymeric coating layer is applied to the core using film coating techniques, the hydrophilic gelling polymer is solubilized in an aqueous solution. Typically, the polymer used for film coating exhibits a viscosity ranging from about 3 to 100 mPa.s. at 25° C. in a 2% aqueous solution.

Although some organic solvents may be employed in the film coating application of the swellable polymeric coating layer, the inclusion of organic solvents in the film coating solution utilized in the methods of the present invention is not required.

The solution of hydrophilic gelling polymer can be applied to the core by any means of film coating including but not limited to fluid bed, or pan coating. Preferably, the solution of polymer is sprayed on the core to form the swellable polymeric coating layer.

The polymer is applied on the core in order to build the desired thickness of the swellable polymeric coating layer. For example, in the embodiment wherein film coating is employed, the core is sprayed with the solution of polymer until the desired thickness of swellable polymeric coating layer is achieved. The desired thicknesses are the same as described above for the alternate method or preparing these formulations.

The methods of the present invention provide a time-specific dosage formulation which is suitable for oral administration and delivery in the gastro-intestinal tract. The formulation includes (a) a core comprising the pharmaceutically active agent, and (b) a swellable polymeric coating layer substantially surrounding the core. In one embodiment the core comprises a solid, tablet-like core. In another embodiment, the core comprises a liquid-filled capsule core. As described hereinabove, the swellable polymeric coating layer is applied or provided by alternately wetting the core with a binder solution and coating the core with powdered polymeric particles a sufficient number of times to produce a time-specific dosage formulation having the desired thickness of swellable polymeric coating layer. The number of alternate wetting and coating processes depends upon the desired thickness of the coating layer, which in turn determines the lag time within the body after administration, prior to delivery of the pharmaceutically active agent.

Accordingly the methods of the present invention also include methods of achieving the time-specific delivery of a pharmaceutically active agent to a patient in need of the therapeutic effects of the pharmaceutically active agent. The method includes administering to the patient the time-specific release dosage form described hereinabove.

Suitable patient populations for which the methods of the present invention are directed include mammals in general, and in particular, humans.

The following examples are provided to illustrate the present invention, and should not be construed as limiting thereof. In these examples, "μg" means micrograms, "mg" means milligrams, "g" means grams, "mm" means millimeters, "μm" means micrometers, "kp" means 9.807 Newton, "mPa.s" means millipascal per second, "min." means minute(s), and "° C." means degrees Centigrade. All percentages are in percent by weight of the tablet unless otherwise indicated. Disintegration tests are carried out according to the standard procedures set forth in the United States Pharmacopoeia for testing the disintegration of tablets.

EXAMPLE 1

Diclofenac sodium (25 mg), 140 mg of dibasic calcium phosphate dihydrate, 24 mg of microcrystalline cellulose, and 10 mg of sodium starch glycolate, are mixed thoroughly. Magnesium stearate (1 mg) is added and thoroughly mixed for another 5 min. The granular mixture is formed into tablet cores of 6.8 mm diameter, weighing 200 mg each, using a rotary tablet press. The cores show a disintegration time lower than 5 min. in water, a Schleuninger hardness higher than 10 kp and a friability lower than 0.1%.

The cores are heated to 40° C. and the coating layer is applied onto the cores in a two-step procedure, using an automatic coating pan. In the first step, the cores are wetted with a binder solution including 15% polyvinylpyrrolidone, and 85% purified water. In the second step, the wetted cores are treated with a dry mixture including 22.5% METHOCEL E5®, 67.5% METHOCEL K15M, 9% talc and 1% colloidal silicon dioxide. Steps 1 and 2 are repeated until a weight gain corresponding to 30% of total tablet weight is achieved. The time necessary to apply a weight gain of 30% has been less than 3 hours.

The coated tablets show a dissolution time lag in excess of 302±56 min, indicating that there is no release of diclofenac from the core in the first 5 hours.

EXAMPLE 2

Comparative Example -Spray Coating

Cores (20,000) containing 25 mg diclofenac sodium are prepared according to Example 1.

The cores are heated to 40° C. and the coating layer is applied by continuously spraying the cores with a solution including 7.5% METHOCEL E50®, 0.5% PEG 6000®, and 92% purified water. until a weight gain corresponding to 60% of the tablet weight is achieved. The coating time corresponds to 5 days.

The coated tablets show a dissolution time lag in excess of 300 min., followed by a quick disintegration of the tablet.

EXAMPLE 3

Verapamil HCl (40 mg), 129 mg of dibasic calcium phosphate dihydrate, 20 mg of microcrystalline cellulose, and 10 mg of sodium starch glycolate, are mixed thoroughly. Magnesium stearate (1 mg) is added and thoroughly mixed for another 5 min. The granular mixture is formed into tablet cores of 6.8 mm diameter, weighing 200 mg each using a rotary tablet press. The cores show a disintegration time lower than 5 min. in water, a Schleuninger hardness higher than 10 kp and a friability lower than 0.1%.

The cores are heated to 40° C. and the coating layer is applied onto the cores in a two-step procedure, using an automatic coating pan. In the first step, the cores are wetted with a binder solution including 5% METHOCEL E5®, 10% polyvinylpyrrolidone, and 85% purified water. In the second step, the wetted cores are treated with a dry mixture including 90% METHOCEL K15M®, 9% talc and 1% colloidal silicon dioxide. Steps 1 and 2 are repeated until a weight gain corresponding to 50% of total tablet weight is achieved.

The coated tablets showed a dissolution time lag in excess of 300 min., followed by a quick disintegration of the tablet.

EXAMPLE 4

Isosorbide-5-mononitrate (20 mg), 135 mg of Lactose S.D. 34 mg of microcrystalline cellulose, and 10 mg of sodium starch glycolate, are mixed thoroughly. Magnesium stearate (1 mg) is added and thoroughly mixed for another 5 min. The granular mixture is formed into tablet cores of 6.8 mm diameter, weighing 200 mg each using a rotary tablet press. The cores show a disintegration time lower than 5 min. in water, a Schleuninger hardness higher than 10 kp and a friability lower than 0.1%.

The cores are heated to 40° C. and the coating layer is applied onto the cores in a two-step procedure, using an automatic coating pan. In the first step, the cores are wetted with a binder solution including 7% METHOCEL E50®, 3% PEG 400®, and 90% purified water. In the second step, the wetted cores are treated with a dry mixture including 90% METHOCEL K15M®, 9% talc and 1% colloidal silicon dioxide. Steps 1 and 2 are repeated until a weight gain corresponding to 70% of total tablet weight is achieved. Samples corresponding to weight gains of 25, 50, and 70% were collected.

The coated tablets showed a disintegration time lag linearly proportional to the amount of coating layer applied, until a time lag corresponding to 8 hours for the last sample.

EXAMPLE 5

Tablet cores containing 1 mg of lorazepam as the active ingredient are heated to 40° C. and coated in a two-step procedure, using an automatic coating pan. In the first step, the cores are wetted with a binder solution including 15% polyvinylpyrrolidone and 85% purified water. In the second step, the wetted cores are treated with a dry mixture including 45% METHOCEL E5®, 45% NATROSOL HHR®, 9% talc and 1% colloidal silicon dioxide. Steps 1 and 2 are repeated until a weight gain corresponding to 35% of total tablet weight is achieved. The coating layer is determined to be approximately 0.7–0.8 mm in thickness. The coating time corresponds to 6 hours. The coated tablets showed a disintegration time lag in excess of 300 min.

EXAMPLE 6

Comparative Example-Fluid Bed Coating

Tablets containing 1 mg of lorazepam are coated with a coating layer using a fluid bed apparatus. The cores are heated to 40° C. and the coating layer is applied by continuously spraying a solution including 7.5% METHOCEL E50®, 0.5% PEG 6000®, 1% colloidal silicon dioxide, and 91% purified water, until a layer corresponding to 50% of weight gain is applied. The coating time corresponds to 5 days. The coated tablets showed a disintegration time lag in excess of 300 min.

EXAMPLE 7

Bromocryptine mesylate (2.87 mg), 30 mg of microcrystalline cellulose, and 2 mg of maleic acid are mixed thoroughly. Lactose S.D. (153.78 mg), 10 mg of sodium starch glycolate, 0.35 mg colloidal silicon dioxide, and magnesium stearate (1 mg) are added and thoroughly mixed for another 10 min. The granular mixture is formed into tablet cores of 6.8 mm diameter, weighing 200 mg using a rotary tablet press. The cores show a disintegration time lower than 5 min. in water, a Schleuninger hardness higher than 10 kp and a friability lower than 0.1%.

The cores are heated to 40° C. and the coating layer is applied onto the cores in a two-step procedure, using an automatic coating pan. In the first step, the cores are wetted with a binder solution including 7% METHOCEL E50®, 3% PEG 400®, and 90% purified water. In the second step, the wetted cores are treated with a dry mixture including 90% METHOCEL K15M®, 9% talc and 1% colloidal silicon dioxide. Steps 1 and 2 are repeated until a weight gain corresponding to 50% of total tablet weight is achieved. The coated tablets showed a disintegration time lag in excess of 5 hours.

EXAMPLE 8

Sugar pellets (15 kg) having a diameter of 0.4–0.6 mm were increased with diclofenac sodium, in a two-step procedure using an automatic rotary pan. First, the pellets are wetted with a 30% aqueous suspension of acrylic and methacrylic copolymer soluble in gastric medium. Second, the wetted pellets are treated with a dry mixture including 90.1% diclofenac sodium, 9% talc, and 0.9% colloidal silicon dioxide. These steps are repeated until a diclofenac sodium potency of 50% is achieved.

The core pellets are coated with the coating layer in a two-step procedure, using an automatic coating pan. In the first step, the core pellets are wetted with a binder solution including 15% polyvinylpyrrolidone and 85% purified water. In the second step, the wetted core pellets are treated with a dry mixture including 80% METHOCEL K15M®, and 20% talc. Steps 1 and 2 are repeated until a weight gain corresponding to 75% of total pellet weight is achieved. An amount of coated pellets corresponding to 100 mg of diclofenac sodium is encapsulated in a hard shell gelatin capsule to provide a single dosage form. The capsule showed a disintegration time lag in excess of 6 hours.

EXAMPLE 9

Cyclosporin A (100 mg), 140 mg dibasic calcium phosphate dihydrate, 25 mg of microcrystalline cellulose, 11 mg of sodium starch glycolate, and 0.5 mg of colloidal silicon dioxide are mixed thoroughly. Glyceryl behenate (3.5 mg) is added and thoroughly mixed for another 5 min. The granular mixture is formed into tablet cores of 8.7 mm diameter, weighing 280 mg using a rotary tablet press. The cores show a disintegration time lower than 5 min. in water, a Schleuninger hardness higher than 10 kp and a friability lower than 0.1%.

The cores are heated to 40° C. and the coating layer is applied onto the cores in a two-step procedure, using an automatic coating pan. In the first step, the cores are wetted with a binder solution including 15% polyvinylpyrrolidone, and 85% purified water. In the second step, the wetted cores are treated with a dry mixture including 45% METHOCEL E5®, 45% METHOCEL K15M®, 9% talc and 1% colloidal silicon dioxide. Steps 1 and 2 are repeated until a weight gain corresponding to 50% of total tablet weight is achieved. The coated tablets showed a disintegration time lag in excess of 6 hours.

EXAMPLE 10

Insulin (100 I.U.), aprotinin (100,000 I.U.), poloxamer F127 (45 mg), purified water (15 mg), PEG-8 caprylic/capric glycerides (90 mg), and isopropyl myristate (q.s. to 300 mg) are mixed until solubilization.

The obtained solution is dosed into 5 oval-shaped soft gelatin capsules formed from gelatin (106.0 mg), glycerin (41.7 mg), red iron oxide (1.7 mg), sodium ethyl paraben (0.4 mg), and sodium propylparaben (0.2 mg).

The capsules show a disintegration time lower than 5 min. in water.

The capsules are heated to 35° C. and the coating layer is applied onto the cores in a two-step procedure, using an automatic coating pan. In the first step, the cores are wetted with a binder solution including 5% METHOCEL E5®, 0.5% gelatin, and 94.5% purified water. In the second step, the wetted cores are treated with a dry mixture including 90% METHOCEL K15M®, 9% talc and 1% colloidal silicon dioxide. Steps 1 and 2 are repeated until a weight gain corresponding to 30% of total capsule weight is achieved.

The coated capsules showed a dissolution time in excess of 240 min., followed by a quick disintegration of the capsule.

EXAMPLE 11

Cyclosporin A (100 mg), ethyl alcohol (80 mg), poloxamer F127 (75 mg), purified water (25 mg), cocamide DEA (85 mg), and isopropyl myristate (135 mg) are mixed until solubilization.

The obtained microemulsion is dosed into 8 oblong-shaped, soft gelatin capsules, formed from gelatine (216.9 mg), glycerin (3.7 mg), sorbitol 70% (75.9 mg), and titanium dioxide (3.5 mg).

The capsules are heated to 30–35° C. and coated in a two-step procedure, using an automatic coating pan. In the first step, the capsules are wetted with a binder solution including 15% polyvinylpyrrolidone, 1% gelatin, and 84% purified water. In the second step, the wetted cores are treated with a dry mixture including 45% METHOCEL E5®, 45% METHOCEL K15M®, 9% talc, and 1% colloidal silicon dioxide. Steps 1 and 2 are repeated until a weight gain corresponding to 50% of total capsule weight is achieved. The coated capsules showed a disintegration time lag in excess of 5 hours.

EXAMPLE 12

The capsules of Example 11 are heated to 30–35° C. and coated by continuously spraying a solution including 7.5% METHOCEL E50®, 0.5% PEG 6000, 1% colloidal silicon dioxide, and 91% purified water, until a weight gain corresponding to 30% of total capsule weight is achieved. The coated capsules showed a disintegration time lag in excess of 240 min.

EXAMPLE 13

Etoposide (50 mg), ethoxydiglycol (86.5 mg), apricot kernel oil PEG-6 esters (27.9 mg), caprylic/capric triglyceride (55.9 mg), polyglyceryl-6 isostearate (72.6 mg), PEG-8 caprylic/capric glycerides (251.3 mg), and purified water (55.8 mg) are mixed until solubilized in the form of a microemulsion.

The obtained microemulsion is dosed into 10 oval-shaped, soft gelatin capsules, formed from gelatin (185 mg), glycerol (90 mg), sodium ethyl paraben (0.8 mg), sodium propylparaben (0.4 mg), titanium dioxide (2.7 mg), yellow iron oxide (0.2 mg), PEG 20000 (7 mg), and PEG 1550 (3 mg).

The capsules are heated to 30–35° C. and the coating layer is applied onto the capsules in a two-step procedure, using an automatic coating pan. In the first step, the capsules are wetted with a binder solution including 7% METHOCEL E50®, 3% PEG 400, and 90% purified water. In the second step, the wetted capsules are treated with a dry mixture including 22.5% METHOCEL E5®, 67.5% METHOCEL K15M®, 9% talc, and 1% colloidal silicon dioxide. Steps 1 and 2 are repeated until a weight gain corresponding to 30% of total capsule weight is achieved. The coated capsules show a dissolution time lag in excess of 240 min.

EXAMPLE 14

*Staphylococcus aureus* (2 mg, corresponding to $10^9$ bacteria), *Echerichia coli* (2 mg, corresponding to $10^9$ bacteria), *Aerobacter aerogenes* (2 mg, corresponding to $10^9$ bacteria), *Proteus vulgaris* (2 mg, corresponding to $10^9$ bacteria), and PEG 400 are mixed thoroughly.

The obtained dispersion is dosed into 3 oval-shaped, soft gelatin capsules, formed from gelatin (67 mg), glycerin (33 mg), sodium ethyl paraben (0.3 mg), sodium propylparaben (0.2 mg), and E127 (0.02 mg).

The capsules are heated to 30° C. and the coating layer is applied onto the capsules in a two-step procedure, using an automatic coating pan. In the first step, the capsules are wetted with a binder solution including 15% polyvinylpyrrolidone, and 85% purified water. In the second step, the wetted capsules are treated with a dry mixture including 45% METHOCEL E5®, 45% NATROSOL HHR®, 9% talc, and 1% colloidal silicon dioxide. Steps 1 and 2 are repeated until a weight gain corresponding to 30% of total capsule weight is achieved. The coated capsules showed a disintegration time lag in excess of 240 min.

EXAMPLE 15

Salmon calcitonin (500 I.U.), sodium methylparaben (1.5 mg), disodium edetate (10.3 mg), sodium cholate (10.3 mg), and purified water (40.6 mg) are solubilized, and the temperature increase to 60° C.

Egg phosphatidylcholine (38.6 mg), cholesterol (7.8 mg), ethyl alcohol (61.7 mg), and tocopherol acetate (0.2 mg) are solubilized, and the temperature increased to 60° C.

The obtained liposome dispersion is dosed into 3 oval soft gelatin capsules, formed by gelatin (67 mg), glycerin (33 mg), sodium ethyl paraben (0.3 mg), sodium propylparaben (0.2 mg), and E127 (0.02 mg).

The capsules are heated to 25–30° C. and the coating layer is applied onto the cores in a two-step procedure, using an automatic coating pan. In the first step, the capsules are wetted with a binder solution including 7% METHOCEL E50®, 3% PEG 400, 70% ethyl alcohol, and 20% purified water. In the second step, the wetted cores are treated with a dry mixture including 90% METHOCEL K15M®, 9% talc, and 1% colloidal silicon dioxide. Steps 1 and 2 are repeated until a weight gain corresponding to 30% of total capsule weight is achieved. The coated capsules showed a disintegration time lag in excess of 240 min.

The foregoing is illustrative of the present invention and is not to be construed as limiting thereof. The invention is defined by the following claims, with equivalents of the claims to be included therein.

That which is claimed is:

1. A method for time-specific delivery of a pharmaceutically active agent to a patient in need of the therapeutic effects of said pharmaceutically active agent, said method comprising administering to said patient, a pharmaceutical formulation comprising:

(a) a core which comprises a capsule containing a liquid form of said pharmaceutically active agent, and (b) a swellable polymeric coating layer substantially surrounding said core, that delays the release of said pharmaceutically active agent from said core for a predetermined period of time dependent upon the thickness of said swellable polymeric coating layer; and wherein said swellable polymeric coating layer is provided by alternately (I) wetting said core with a binder solution, and (ii) coating said core with powdered polymeric particles a sufficient number of times to produce a time-specific dosage formulation having the desired thickness of swellable polymeric coating layer.

2. The method according to claim 1, wherein said pharmaceutical formulation is administered orally.

3. The method according to claim 1, wherein said liquid form of said pharmaceutically active agent is selected from the group consisting of solutions, liposome dispersions, oil-in-water emulsions, microemulsions, precursors of microemulsions and liposomes, dispersions of microparticles, dispersions of nanoparticles, dispersions of solid lipid nanoparticles, and suspensions.

4. The method according to claim 1, wherein said pharmaceutically active agent is selected from the group consisting of steroids, xanthines, beta-2-agonist bronchodilators, anti-inflammatory agents, analgesic agents, calcium antagonists, angiotensin-converting enzyme inhibitors, beta-blockers, centrally active alpha-agonists, alpha-1-antagonists, anticholinergic/antispasmodic agents, vasopressin analogues, antiarrhythmic agents, antiparkinsonian agents, antiangina/antihypertensive agents, anticoagulant agents, antiplatelet agents, sedatives, ansiolytic agents, peptidic agents, biopolymeric agents, antineoplastic agents, laxatives, antidiarrheal agents, antimicrobial agents, antifungal agents, vaccines, and nucleic acids.

5. The method according to claim 1, wherein said swellable polymeric coating layer comprises powdered polymeric particles selected from the group consisting of hydroxypropylmethylcellulose, hydroxyethylcellulose, hydroxypropylcellulose, polyvinylpyrrolidone, polyvinyl alcohol, acrylic acid polymer, methacrylic acid copolymers, ethyl acrylate-methyl methacrylate copolymers, and mixtures thereof.

6. The method according to claim 1, wherein said binder solution is selected from the group consisting of polyvinylpyrrolidone, hydroxypropylmethylcellulose, polyvinyl alcohol, hydroxyethylcellulose, methacrylic acid copolymers, ethylacrylate-methylmethacrylate copolymers, guar gum, arabic gum, xanthan gum, gelatin, pectin, and mixtures thereof.

7. The method according to claim 1, wherein said swellable polymeric coating layer comprises polymeric hydroxypropylmethylcellulose particles.

8. The method according to claim 1, wherein said binder solution is polyvinylpyrrolidone.

9. The method according to claim 1, wherein said swellable polymeric coating layer is not less than 50 $\mu$m thick.

10. The method according to claim 1, wherein said swellable polymeric coating layer is sufficiently thick to achieve a core:coating layer ratio of between about 20:1 to about 1:5.

11. The method according to claim 1, wherein said swellable polymeric coating layer is sufficiently thick to achieve a core:coating layer ratio of between about 5:1 to about 1:3.

12. A method for time-specific delivery of a pharmaceutically active agent to a patient in need of the therapeutic effects of said pharmaceutically active agent, said method comprising administering to said patient, a pharmaceutical formulation comprising:

(a) a core which comprises a capsule containing a liquid form of said pharmaceutically active agent, and (b) a swellable polymeric coating layer substantially surrounding said core, that delays the release of said pharmaceutically active agent from said core for a predetermined period of time dependent upon the thickness of said swellable polymeric coating layer; and wherein said swellable polymeric coating layer is formed from powdered polymeric particles.

13. A method for producing a time-specific dosage formulation for time-specific delivery of a pharmaceutically active agent, said method comprising coating a core which comprises a capsule containing a liquid form of said pharmaceutically active agent, with a swellable polymeric coating layer that delays the release of said pharmaceutically active agent from said core for a predetermined period of time dependent upon the thickness of said swellable polymeric coating layer; wherein said step of coating said core with said swellable polymeric coating layer comprises alternately (I) wetting said core with a binder solution, and (ii) coating said core with powdered polymeric particles a sufficient number of times to produce a time-specific dosage formulation having the desired thickness of swellable polymeric coating layer.

14. The method according to claim 13 further comprising the steps of (1) providing a liquid form of said pharmaceutically active agent selected from the group consisting of solutions, liposome dispersions, oil-in-water emulsions, microemulsions, precursors of microemulsions and liposomes, dispersions of microparticles, dispersions of nanoparticles, dispersions of solid lipid nanoparticles, and suspensions, and (2) encapsulating said liquid form of said pharmaceutically active agent in a capsule, prior to said step of coating said core.

15. The method according to claim 13, wherein said pharmaceutically active agent is selected from the group consisting of steroids, xanthines, beta-2-agonist bronchodilators, anti-inflammatory agents, analgesic agents, calcium antagonists, angiotensin-converting enzyme inhibitors, beta-blockers, centrally active alpha-agonists, alpha-1-antagonists, anticholinergic/antispasmodic agents, vasopressin analogues, antiarrhythmic agents, antiparkinsonian agents, antiangina/antihypertensive agents, anticoagulant agents, antiplatelet agents, sedatives, ansiolytic agents, peptidic agents, biopolymeric agents, antineoplastic agents, laxatives, antidiarrheal agents, antimicrobial agents, antifungal agents, vaccines, and nucleic acids.

16. The method according to claim 13, wherein said swellable polymeric coating layer comprises powdered polymeric particles selected from the group consisting of hydroxypropylmethylcellulose, hydroxyethylcellulose, hydroxypropylcellulose, polyvinylpyrrolidone, polyvinyl alcohol, acrylic acid polymer, methacrylic acid copolymers, ethyl acrylate-methyl methacrylate copolymers, and mixtures thereof.

17. The method according to claim 13, wherein said binder solution is selected from the group consisting of polyvinylpyrrolidone, hydroxypropylmethylcellulose, polyvinyl alcohol, hydroxyethylcellulose, methacrylic acid copolymers, ethylacrylate-methylmethacrylate copolymers, guar gum, arabic gum, xanthan gum, gelatin, pectin, and mixtures thereof.

18. The method according to claim 13, wherein said step of coating said core with said swellable polymeric coating layer comprises coating said core with a swellable polymeric coating layer not less than 50 $\mu$m thick.

19. The method according to claim 13, wherein said step of coating said core with said swellable polymeric coating layer comprises coating said core with a swellable polymeric coating layer to achieve a core:coating layer ratio of between about 20:1 to about 1:5.

20. A pharmaceutical formulation for the time-specific delivery of a pharmaceutically active agent, said formulation comprising:

(a) a core comprising a capsule containing a liquid form of said pharmaceutically active agent, and (b) a swellable polymeric coating layer substantially surrounding said core, wherein said swellable polymeric coating layer delays the release of said pharmaceutically active agent from said core for a predetermined period of time dependent upon the thickness of said swellable polymeric coating layer; and wherein said swellable polymeric coating layer is provided by alternately (I) wetting said core with a binder solution, and (ii) coating said core with powdered polymeric particles a sufficient number of times to produce a time-specific dosage formulation having the desired thickness of swellable polymeric coating layer.

* * * * *